United States Patent
Yukumoto et al.

(10) Patent No.: US 9,242,907 B2
(45) Date of Patent: Jan. 26, 2016

(54) BIOMASS GASIFICATION GAS PURIFICATION SYSTEM AND METHOD, AND METHANOL PRODUCTION SYSTEM AND METHOD

(75) Inventors: Atsuhiro Yukumoto, Tokyo (JP); Wataru Matsubara, Tokyo (JP); Shinya Tachibana, Tokyo (JP); Toshiya Akiba, Tokyo (JP); Katsuhiko Shinoda, Tokyo (JP); Takeshi Amari, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 437 days.

(21) Appl. No.: 13/807,163

(22) PCT Filed: Aug. 3, 2011

(86) PCT No.: PCT/JP2011/067797
§ 371 (c)(1),
(2), (4) Date: Dec. 27, 2012

(87) PCT Pub. No.: WO2012/020684
PCT Pub. Date: Feb. 16, 2012

(65) Prior Publication Data
US 2013/0109766 A1 May 2, 2013

(30) Foreign Application Priority Data
Aug. 9, 2010 (JP) ................. 2010-179081

(51) Int. Cl.
*C07C 27/00* (2006.01)
*B01J 8/00* (2006.01)
(Continued)

(52) U.S. Cl.
CPC . *C07C 1/12* (2013.01); *B01J 12/00* (2013.01); *C01B 3/38* (2013.01); *C07C 29/1518* (2013.01);
(Continued)

(58) Field of Classification Search
CPC ............... C01B 2203/142; Y02E 50/32; C10J 2300/1853; C10J 2300/1665; C10J 2300/0916; C07C 31/04; C07C 29/1518; C10K 3/023; C10K 1/02; C10K 1/004
USPC ................................ 518/700, 702; 423/245.1
See application file for complete search history.

(56) References Cited

U.S. PATENT DOCUMENTS 6,991,769 B2   1/2006 Kaneko et al.
2007/0051043 A1  3/2007 Schingnitz et al.
(Continued)

FOREIGN PATENT DOCUMENTS

EP   1431373 A1   6/2004
JP   2001-240877 A   9/2001
(Continued)

OTHER PUBLICATIONS

U.S. Office Action dated Jul. 16, 2014, issued in U.S. Appl. No. 13/702,810.( 17 pages).
(Continued)

*Primary Examiner* — Jafar Parsa
(74) *Attorney, Agent, or Firm* — Westerman, Hattori, Daniels & Adrian, LLP (57) ABSTRACT

A biomass gasification gas purification system has a dust removal apparatus for filtering soot and dust from biomass gasification gas (including tar component) obtained through the gasification of the biomass using a biomass gasification furnace, a desulfurization apparatus for removing sulfur oxide component in the filtered biomass gasification gas, first to third pre-reformation reactors that provide pre-reforming catalyst for reforming the tar component in the biomass gasification gas after desulfurization, and first and second coolers that are interposed between the first to third pre-reformation reactors, and for cooling the reformed gas.

3 Claims, 5 Drawing Sheets

(51) Int. Cl.

| | | |
|---|---|---|
| *C07C 1/12* | (2006.01) | |
| *C10K 1/00* | (2006.01) | |
| *C10K 1/02* | (2006.01) | |
| *C10K 3/02* | (2006.01) | |
| *B01J 12/00* | (2006.01) | |
| *C07C 29/151* | (2006.01) | |
| *C10J 3/84* | (2006.01) | |
| *C01B 3/38* | (2006.01) | |

(52) U.S. Cl.
 CPC . *C10J 3/84* (2013.01); *C10K 1/004* (2013.01); *C10K 1/02* (2013.01); *C10K 1/024* (2013.01); *C10K 3/023* (2013.01); *C01B 2203/0233* (2013.01); *C01B 2203/0445* (2013.01); *C01B 2203/061* (2013.01); *C01B 2203/107* (2013.01); *C01B 2203/1058* (2013.01); *C01B 2203/1258* (2013.01); *C01B 2203/142* (2013.01); *C01B 2203/143* (2013.01); *C01B 2203/1619* (2013.01); *C10G 2300/1011* (2013.01); *C10J 2300/0916* (2013.01); *C10J 2300/1665* (2013.01); *C10J 2300/1853* (2013.01); *Y02E 50/18* (2013.01); *Y02E 50/32* (2013.01)

(56) References Cited

U.S. PATENT DOCUMENTS

| | | |
|---|---|---|
| 2010/0249251 A1 | 9/2010 | Hilton |
| 2011/0314736 A1 | 12/2011 | Crespin |
| 2013/0085307 A1 | 4/2013 | Yukumoto et al. |

FOREIGN PATENT DOCUMENTS

| | | |
|---|---|---|
| JP | 2001-240878 A | 9/2001 |
| JP | 2004-346285 A | 12/2004 |
| JP | 2006-016470 A | 1/2006 |
| JP | 2006-348155 A | 12/2006 |
| JP | 2007-204558 A | 8/2007 |
| JP | 2009-040862 A | 2/2009 |
| JP | 2009-536262 A | 10/2009 |
| JP | 2009-279473 A | 12/2009 |
| JP | 2010-077219 A | 4/2010 |
| JP | 2010-111779 A | 5/2010 |
| WO | 99/41329 A1 | 8/1999 |
| WO | 03/018467 A2 | 3/2003 |
| WO | 2007/131240 A2 | 11/2007 |
| WO | 2010/035430 A1 | 4/2010 |

OTHER PUBLICATIONS

Roberto Coll et al; "Steam reforming model compounds of biomass gasification tars: conversion at different operating conditions and tendency towards coke formation", Fuel Processing Technology, vol. 74 (2001) pp. 19-31.
US Notice of Allowance dated Nov. 18, 2014, issued in corresponding U.S. Appl. No. 13/702,810 (10 pages).
English Translation of Written Opinion of PCT/JP2011/067797, mailing date Sep. 6, 2011. (4 pages).
Written Opinion of PCT/JP2011/067797, mailing date of Sep. 6, 2011.
International Search Report for PCT/JP2011/067797, mailing date of Sep. 6, 2011.
Japanese Decision of a Patent Grant dated Feb. 12, 2014, issued in corresponding Japanese Patent Application No. 2010-179081 with English translation (3 pages).
Japanese Decision of a Patent Grant dated Apr. 1, 2014, issued in related Japanese Patent Application No. 2010-179080 with English translation (4 pages).
Extended European Search Report dated Apr. 16, 2014, issued in related European Patent Application No. 11816351.8 (7 pages).
Hiller et al., "Gas Production, 5.4. Absorption Processes", Internet Citation, 2006, pp. 1, 90-118, 162, XP-002595382, Retrieved from the Internet: URL:http://mrw.intersciencewiley.com/emrw/9783527306732/ueic/article/a12_169/current/pdf, cited in the Extended European Search Report dated Apr. 16, 2014.
Hamelinck et al., "Future prospects for production of methanol and hydrogen from biomass", Journal of Power Sources, 2002, vol. 111, No. 1, pp. 1-22, XP004380118, cited in the Extended European Search Report dated Apr. 16, 2014.
Extended European Search Report dated Apr. 16, 2014, issued in corresponding European Patent Application No. 11815350.0 (8 pages).
Tatsumi, K. et al. Patent No. JP2010111779A; May 20, 2010; English translation.
English translation of International Search Report issued Sep. 6, 2011 in International (PCT) Application No. PCT/JP2011/067798(corresponding to U.S. Appl. No. 13/702,810).
English translation of Written Opinion of the International Searching Authority issued Sep. 6, 2011 in International (PCT) Application No. PCT/JP2011/067798(corresponding to U.S. Appl. No. 13/702,810).

BIOMASS GASIFICATION GAS PURIFICATION SYSTEM AND METHOD, AND METHANOL PRODUCTION SYSTEM AND METHOD

FIELD

The present invention relates to a biomass gasification gas purification system and method, and a methanol production system and method.

BACKGROUND

The invention relates to a biomass gasification gas purification system and method, and a methanol production system and method, which effectively use biomass as a raw material and may obtain a clean gas raw material available for use as fuel or for production of liquid fuel such as alcohol.

Generally, biomass is biological objects (for example, agricultural products or by-products, wood, plants and the like) available for use as an energy source or an industrial raw material and is generated by action of solar energy, air, water, soil or the like and then is infinitely renewable.

The production of clean energy sources such as gas and methanol for fuel is available by using the biomass described above. In addition, since biomass as waste matter can be processed, it helps to purify the environment and the biomass, which is newly produced, is also grown by photosynthesis while fixing $CO_2$. Since $CO_2$ does not increase in the atmosphere, this leads to restraints on $CO_2$ and is a favorable technique.

Here, as the biomass which is supplied, it is preferable that produced or discarded biomass, which is crushed and dried, be supplied. The biomass in the invention is a biological resource (for example, agricultural products or by-products, wood, plants and the like) available for use as the energy source or the industrial raw material, and for example, plants such as sweet sorghum, napier grass and spirulina, and wood such as Japanese cedar, broad-leaf tree and bark may be used (see Patent Literature 1 and 2, and Non Patent Literature 1).

However, since the gas generated using biomass as the raw material includes fine particles, a tar component, hydrogen sulfide, chlorine or the like, it is not suitable for the gas without modification to synthesize the energy source to liquid fuel and fuel cell using a synthetic catalyst. Thus, as described above, a scheme is devised to remove minor components such as the fine particles, the tar component, the hydrogen sulfide and the chlorine described above, using a gas purification apparatus including a separation apparatus. In the gas as the raw material for obtaining the liquid fuel or the fuel cell described above form the energy source, in practical application, it is necessary for the minor components to be reduced to a permissible content of less than 0.1 mg/Nm³ of tar and less than 0.1 ppm of an S component. However, currently, the biomass gasification system does not lead to a sufficient reduction in the minor components described above.

In addition, a treatment scale using the biomass gasification system described above is hundreds of tons/day and is equivalent to a small scale to a middle scale plant compared to a gasification system using conventional fossil fuel. In a small and middle scale gas treatment system described above, it is desirable to include a simple and cheap gas purification line which is a necessary condition in a so-called decentralization plant. Regarding this point, in the biomass gasification system of the related art, a simple and cheap gas purification line is not realized.

In the related art, a biomass gasification system including separation means such as a cyclone to filter dust from a generated gas which is gasified in a biomass gasification furnace, a cooler cooling the gas from which the dust is filtered, and a gas purification apparatus purifying the gas which is cooled is disclosed (Patent Literature 3).

The gas purification apparatus of the biomass gasification gas of the related art is configured in such a manner that the biomass is temporarily stored and the cooled generated gas passing through the cooler is passed through the gas purification apparatus, the tar component included in the cooled generated gas is absorbed onto the gas purification apparatus and as the purification gas, the tar absorbed biomass, which has absorbed the tar is transported to biomass supply means using transportation means.

Further, a fixed layer type removing apparatus having a remover layer removing the tar component is disclosed (Patent Literature 4).

CITATION LIST

Patent Literature

Patent Literature 1: Japanese Laid-open Patent Publication No. 2001-240877
Patent Literature 2: Japanese Laid-open Patent Publication No. 2001-240878
Patent Literature 3: Japanese Laid-open Patent Publication No. 2004-346285
Patent Literature 4: Japanese Laid-open Patent Publication No. 2006-16470

Non Patent Literature

Non Patent Literature 1: "21$^{st}$ Century Energy Biomass Pioneered" Issued Oct. 28, 1998, published Masayasu SAKAI, Morikita Publishing Co., Ltd.

SUMMARY

Technical Problem

However, the suggestion disclosed in Patent Literature 3 has a problem that removal of the tar component using a biomass absorption tower cannot be performed to decrease to a level where degradation of the catalyst is not caused.

In addition, the suggestion disclosed in Patent Literature 4 has a problem that a processing of active carbon, that is a remover to which the tar component is absorbed, is necessary separately.

As a method for removing (dissolving) the tar (hydrocarbon component having a high boiling point), a method, which dissolves the tar with a reforming reaction of formula (1) described below using a pre-reforming catalyst (for example, an Ni-based catalyst or a Ru-based catalyst), may be considered, however, when the biomass gasification gas has an extremely high concentration of CO component and the gas is reacted under a pressure of about 1 MPaG or less and at a temperature of 400° C. to 550° C. that is an optimal reaction temperature of the catalyst, there is a problem that methanation reaction such as the formulas (3) and (4) described below is caused as a side reaction.

The formula (2) synthesizes formulas (3) and (4) which are referred to as shift reaction.

As the pre-reforming catalyst described above, for example, "ReforMax100" (trade name) and "ReforMax100RS, N.E." (trade name) of SUD-CHEMIE CO., "E catalyst" (trade name) and "Ni-3266E" (trade name) of CAMCAT CO., and "RKNGR, AR-401" (trade name) of Topsoe CO., and the like are commercially available.

Since the methanation reaction of the formulas (3) and (4) is an exothermic reaction, in a case of the pre-reformation reactor including an insulation type pre-reforming catalyst, the temperature of the reactor becomes equal to or more than 550° C. which is an appropriate temperature of the pre-reforming catalyst, sintering or coking occurs, and at the same time, thermal runaway may occur such that there is a problem that favorable gas purification cannot be stably performed.

The invention is made in view of the problems described above and an object of the invention is to provide a biomass gasification gas purification system and method, and a methanol production system and method in which a tar component in a generated gas, where the biomass gas is gasified, is effectively reformed and thermal runaway does not occur.

Solution to Problem

According to a first aspect of the present invention in order to solve the above problems, there is provided a biomass gasification gas purification system including: a dust removal apparatus that filters soot and dust from biomass gasification gas obtained through the gasification of the biomass using a biomass gasification furnace; a desulfurization apparatus that removes a sulfur oxide component in the filtered biomass gasification gas; at least two or more pre-reformation reactors that reform the tar component in the biomass gasification gas after desulfurization; and a cooler that is interposed between the pre-reformation reactors and cools the reformed gas.

According to a second aspect of the present invention, there is provided a biomass gasification gas purification system including: a dust removal apparatus that filters soot and dust from biomass gasification gas obtained through the gasification of the biomass using a biomass gasification furnace; a desulfurization apparatus that removes a sulfur oxide component in the filtered biomass gasification gas; at least two or more pre-reformation reactors that reform the tar component in the biomass gasification gas after desulfurization; a cooler that cools a portion of the biomass gasification gas; and a supply line that supplies the cooled biomass gasification gas between the pre-reformation reactors respectively.

According to a third aspect of the present invention, there is provided a methanol production system including: the biomass gasification gas purification system according to the first or second aspect; a booster that boosts the biomass gasification gas after the pre-reforming; and a methanol synthesizer that synthesizes the methanol using the boosted gas after boosting.

According to a fourth aspect of the present invention, there is provided the methanol production system according to the third aspect, further including: a reformation reactor that reforms the boosted gas after boosting.

According to a fifth aspect of the present invention, there is provided a biomass gasification gas purification method including: filtering soot and dust from biomass gasification gas obtained through the gasification of the biomass using a biomass gasification furnace; desulfurizing sulfur oxide component in the filtered biomass gasification gas; reforming the tar component in the biomass gasification gas after desulfurization using at least two or more pre-reforming reactors; and cooling the reformed gas using a cooler that is interposed between the pre-reformation reactors.

According to a sixth aspect of the present invention, there is provided a biomass gasification gas purification method including: filtering soot and dust from biomass gasification gas obtained through the gasification of the biomass using a biomass gasification furnace; removing sulfur oxide component in the filtered biomass gasification gas; reforming the tar component in the biomass gasification gas after desulfurization using at least two or more pre-reforming reactors; and cooling a portion of the biomass gasification gas and supplying the cooled biomass gasification gas between the pre-reformation reactors respectively.

According to a seventh aspect of the present invention, there is provided a methanol production method including: purifying biomass gasification gas using the biomass gasification gas purification method according to the fifth or sixth aspect; boosting the biomass gasification gas after pre-reforming; and synthesizing the methanol using the boosted gas after boosting.

According to a eighth aspect of the present invention, there is provided the methanol production method according to the seventh, further including: reforming the boosted gas after boosting.

Advantageous Effects of Invention

According to the invention, when reforming the tar component in the biomass gasification gas in which concentration of the CO component is high, the methanation reaction, which is a side reaction, is suppressed and the thermal runaway of the reformation reactor is suppressed so that the gas purification of biomass gasification gas may be stably performed.

DESCRIPTION OF EMBODIMENTS

Hereinafter, the invention is described in detail with reference to the drawings. In addition, the invention is not limited to the embodiments. Constituent elements which may be assumed by those skilled in the art or constituent elements which are substantially the same as the embodiments are included in constituent elements of the embodiments described below.

First Embodiment

Figure 1:
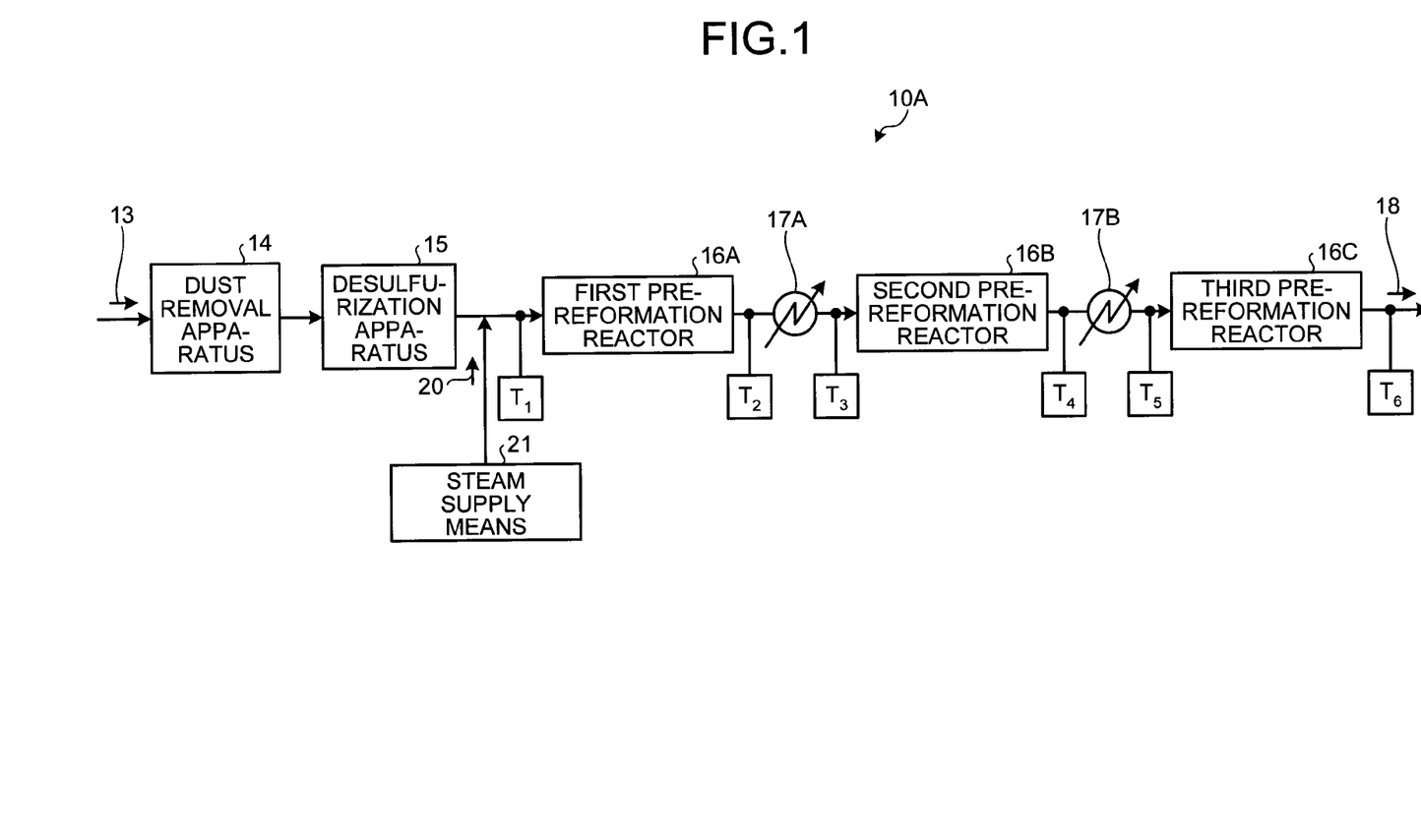
FIG. 1 is a schematic view of a biomass gasification gas purification system according to a first embodiment.

The biomass gasification gas purification system according to the embodiment of the invention is described with reference to the drawings. FIG. 1 is a schematic view of the biomass gasification gas purification system according to the embodiment.

As illustrated in FIG. 1, a biomass gasification gas purification system 10A has a dust removal apparatus 14 that filters soot and dust from biomass gasification gas (including a tar component) 13 obtained through the gasification of biomass using a biomass gasification furnace, a desulfurization apparatus 15 that removes sulfur oxide component in the filtered biomass gasification gas 13, first to third pre-reformation reactors 16A to 16C that provide a pre-reforming catalyst for reforming the tar component in the biomass gasification gas 13 after desulfurization, and first and second coolers 17A and 17B that are interposed between the first to third pre-reformation reactors 16A to 16C, and cool the reformed gas. In addition, in the drawings, reference numeral 18 is a synthesis gas, reference numeral 20 is steam for reforming steam, reference numeral 21 is steam supply means, and reference numerals $T_1$ to $T_6$ are thermometers.

When the biomass gasification gas 13 is introduced into the first pre-reformation reactor 16A after desulfurization, the tar component is reformed and heat is produced. The temperature of the reformed gas is measured with the thermometer $T_2$ of an outlet of the first pre-reformation reactor 16A and the reformed gas is cooled using the first cooler 17A to 4000° C. that is an optimal temperature of the pre-reforming. The second and the third pre-reformation reactors 16B and 16C are also operated in a similar manner and then the gas temperature of the reformed gas is maintained at an appropriate temperature.

In addition, a plurality of pre-reformation reactors are provided so that the capacity of the reactor is for example, between 400° C. to 550° C. that is an optimal temperature of the catalyst considering an amount of heat generation of the pre-reformation reactor including an insulation type pre-reforming catalyst.

In addition, regarding an amount of steam for reforming steam, a ratio of the steam to an amount of carbon in the gas is S/C=3.

As described above, when reforming the tar component including in the biomass gasification gas 13, the pre-reformation reactors are divided into a plurality thereof (in the embodiment, the first to third pre-reformation reactors 16A to 16C) and the first and second coolers 17A and 17B are interposed therebetween so that increase of the temperatures of the first to third pre-reformation reactors 16A to 16C is suppressed and the temperature thereof does not increase to equal to or more than a permissible temperature of the pre-reforming catalyst, and the methanation reaction is suppressed. Furthermore, favorable tar reforming may be performed without occurrence of the sintering or the like due to degradation of the catalyst.

Second Embodiment

Figure 2:
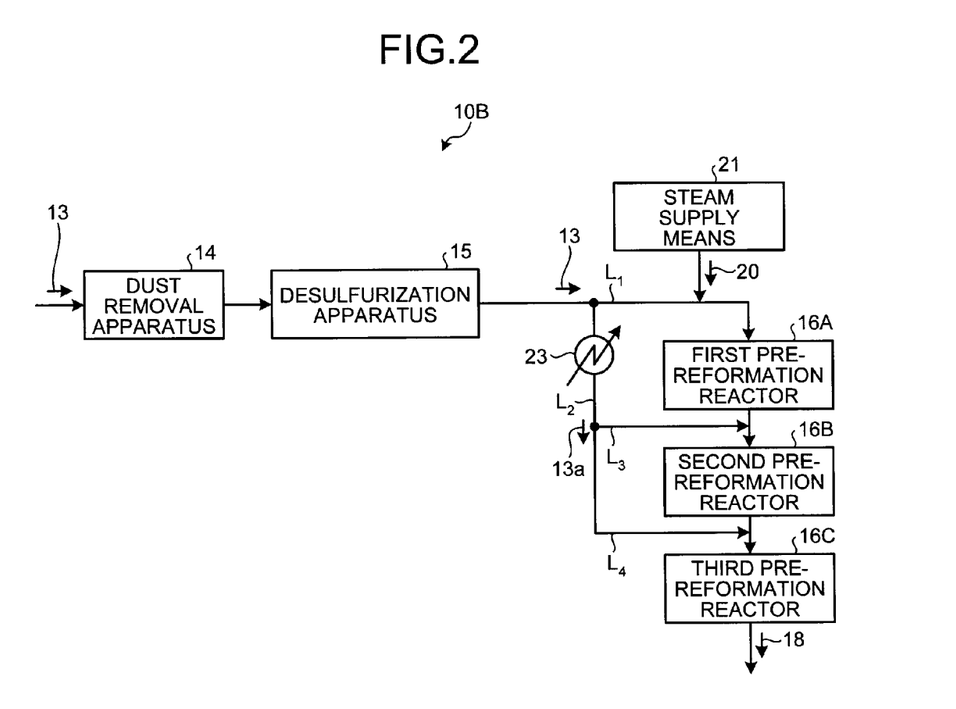
FIG. 2 is a schematic view of a biomass gasification gas purification system according to a second embodiment.

The biomass gasification gas purification system according to the embodiment of the invention is described with reference to the drawings. FIG. 2 is a schematic view of the biomass gasification gas purification system according to the embodiment.

As illustrated in FIG. 2, a biomass gasification gas purification system 10B has the dust removal apparatus 14 that filters soot and dust from biomass gasification gas (including the tar component) 13 obtained through the gasification of the biomass using the biomass gasification furnace, the desulfurization apparatus 15 that removes the sulfur oxide component in the filtered biomass gasification gas 13, the first to third pre-reformation reactors 16A to 16C reforming the tar component in the biomass gasification gas 13 after the desulfurization, and a cooler 23 that is interposed in a diverging line $L_2$, a portion of which is diverged from a supply line $L_1$ of the biomass gasification gas 13 and cools the biomass gasification gas 13 which is diverged, and supply lines $L_3$ and $L_4$ which supply cooled biomass gasification gas 13a between the first to third pre-reformation reactors 16A to 16C respectively.

As described above, when reforming the tar component included in the biomass gasification gas 13, the pre-reformation reactors are divided into a plurality thereof (in the embodiment, the first to third pre-reformation reactors 16A to 16C) and biomass gasification gas 13a, which is cooled using the cooler 23 between them, is supplied via supply lines $L_3$ and $L_4$. Accordingly, increase of the temperature of the first to third pre-reformation reactors 16A to 16C is suppressed, the temperature thereof does not increase to equal to or more than heatproof temperature of the pre-reforming catalyst and the methanation reaction does not progress. Furthermore, the sintering or the like due to the degradation of the catalyst does not occur and favorable tar reformation may be performed.

Figure 3:
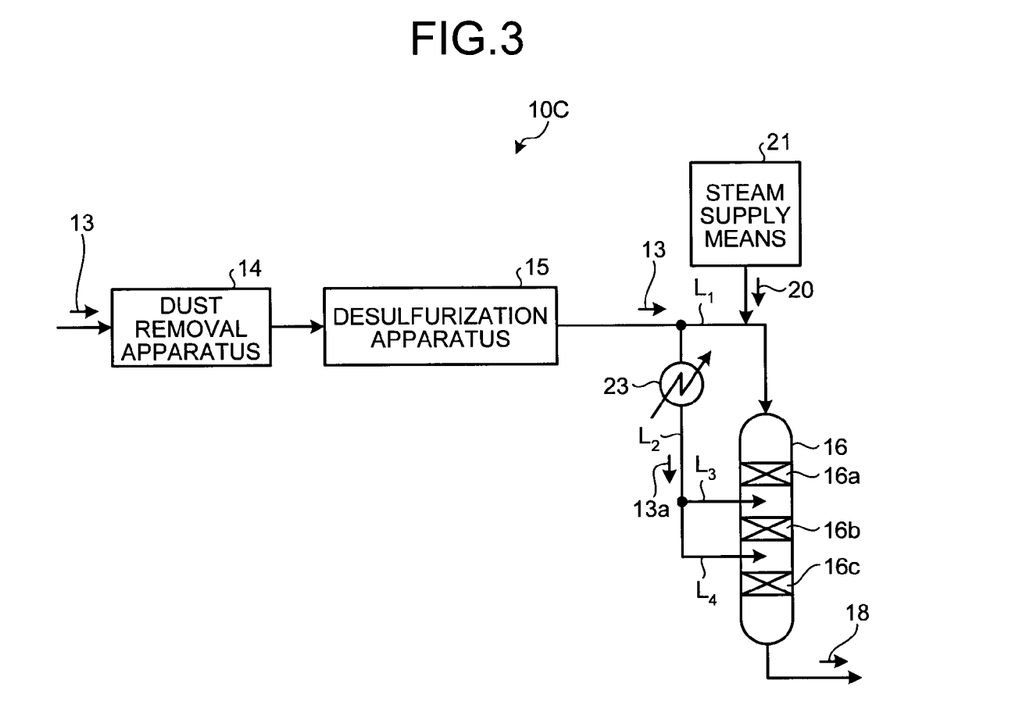
FIG. 3 is a schematic view of another biomass gasification gas purification system according to the second embodiment.

FIG. 3 is a schematic view of another biomass gasification gas purification system according to the embodiment.

As illustrated in FIG. 3, a biomass gasification gas purification system 10C is configured in such a manner that a catalyst zone in a pre-reformation reactor 16 is divided into a plurality of first to third catalyst sections 16a to 16c, and biomass gasification gas 13a cooled using the cooler 23 is supplied between the catalyst sections 16a to 16c respectively via the supply lines $L_3$ and $L_4$. Accordingly, increase of the temperature of the first to third catalyst sections 16a to 16c is suppressed, the temperature thereof does not increase to equal to or more than the heatproof temperature of the pre-reforming catalyst and the methanation reaction does not progress. Furthermore, the sintering or the like due to the degradation of the catalyst does not occur and favorable tar reformation may be performed.

Obtained synthesis gas 18 may be directly used as the fuel gas for the gas turbine. In addition, the gas may be also used as gas for producing chemical products such as ammonia and methanol (or dimethyl ether) by adjusting compositions of $H_2$ and CO gas in the gas. Hereinafter, the system, in which the obtained gas is used in the methanol synthesis, is described.

Third Embodiment

Figure 4:
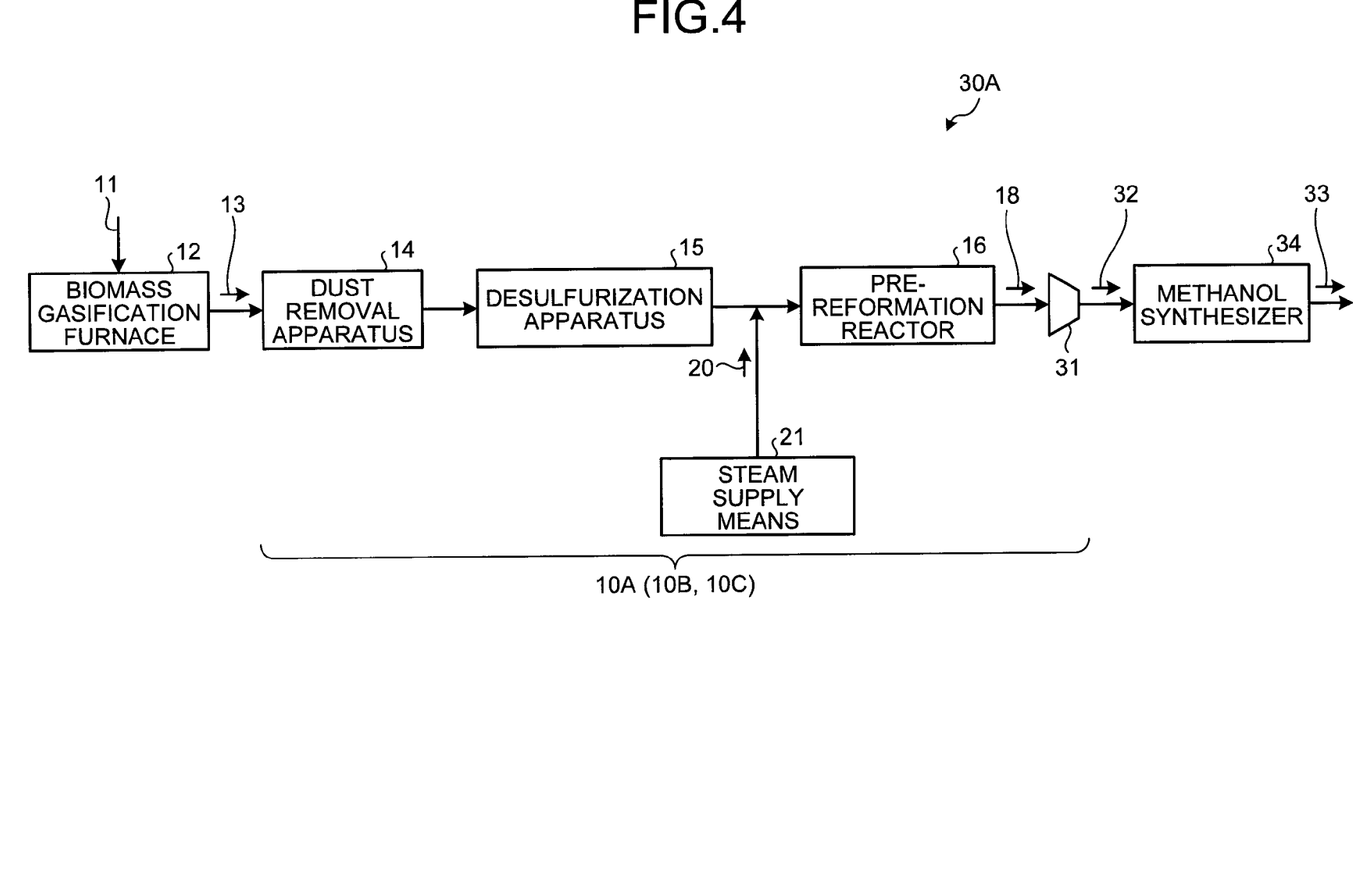
FIG. 4 is a schematic view of a methanol production system according to a third embodiment.
Figure 5:
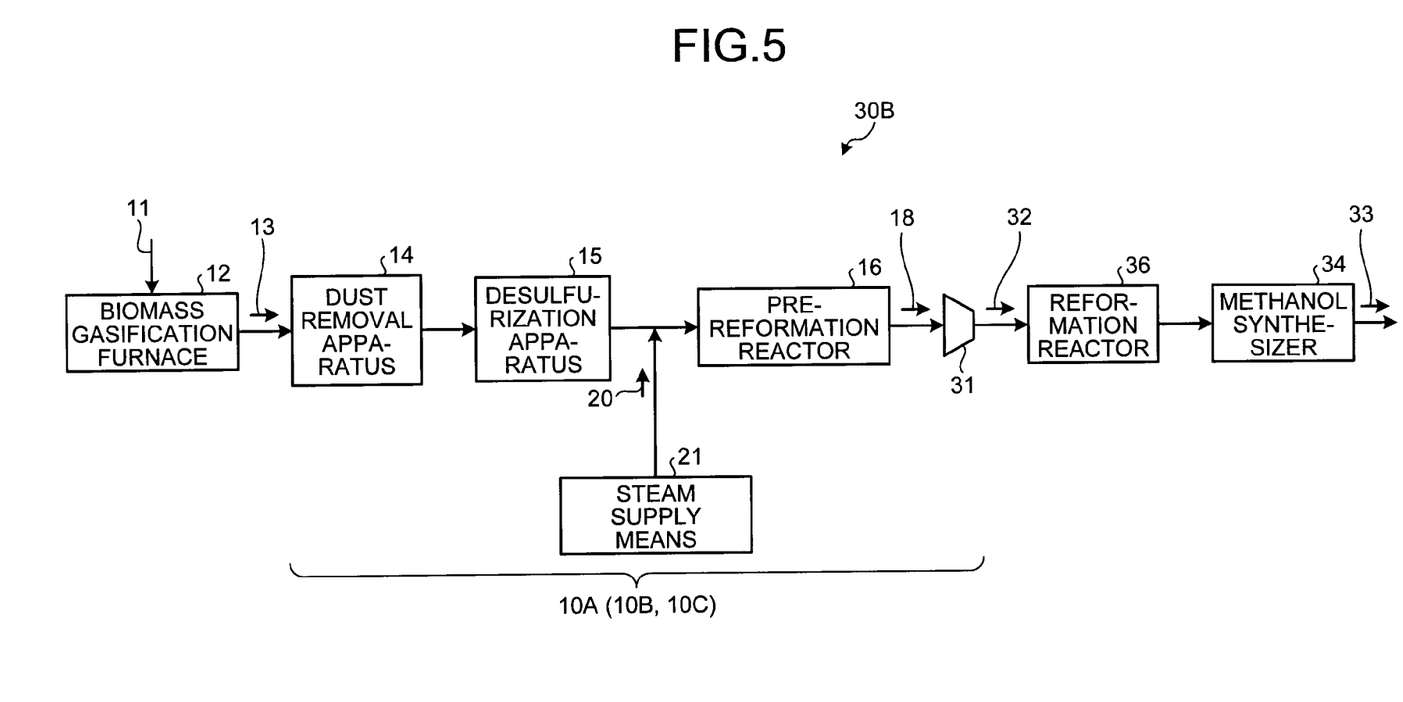
FIG. 5 is a schematic view of another methanol production system according to the third embodiment.

The methanol production system according to the embodiment of the invention is described with reference to the drawings. FIG. 4 is a schematic view of the methanol production system according to the third embodiment. FIG. 5 is a schematic view of another methanol production system according to the third embodiment.

As illustrated in FIG. 4, a methanol production system 30A has a biomass gasification furnace 12 gasifying a biomass 11, the dust removal apparatus 14 that filters soot and dust from the biomass gasification gas (including tar component) 13 obtained through the gasification, the desulfurization apparatus 15 that removes the sulfur oxide component in the filtered biomass gasification gas 13, a pre-reformation reactor 166 reforming the tar component in the biomass gasification gas 13 after desulfurization, a booster 31 which raises the pressure of the synthesis gas 18 of the biomass gasification gas after pre-reforming, and a methanol synthesizer 34 synthesizing methanol 33 using a boosted gas 32 after boosting.

In addition, the biomass gasification gas purification systems 10A (10B and 10C) of the first and second embodiments illustrated in FIGS. 1 to 3 are configured from the dust removal apparatus 14 to the pre-reformation reactor 16. In addition, in the first and second embodiments, the pre-reformation reactor 16 is illustrated as an assembly of the pre-reformation reactors which are divided into plurality thereof and each of cooling means and diverging lines or the like is omitted.

According to the embodiment, when reforming the tar component in the biomass gasification gas 13 in a biomass gasification gas purification system 10, since the tar component is reformed in a predetermined temperature range that is the permissible temperature of the pre-reforming catalyst, the reformation of the tar component may be stably performed and in the gas where the tar component is removed, the methanol synthesis may be stably performed without poisoning the degradation of the methanol synthesis catalyst.

In the invention, as the biomass 11 supplied to the biomass gasification furnace 12, it is preferable that produced or discarded biomass, which is crushed or dried, be supplied. The biomass in the invention is a biological resource (for example, agriculture products or by-products, wood, plants or the like) which is available for use as an energy source or an industrial raw material, and for example, may include plants such as sweet sorghum, napier grass and spirulina, and wood such as Japanese cedar, broad-leaf tree and bark. In the invention, it is preferable that an average particle diameter (D) of the crushed material of the biomass 11 described above be $0.05 \text{ mm} \leq D \leq 5 \text{ mm}$. When the average particle diameter is 0.05 mm or less, crushing efficiency of the biomass is reduced and it is unfavorable. Meanwhile, when the average particle diameter is over 5 mm, favorable combustion is not performed in the inside of the biomass, the reaction is not promoted and thus the gasification is not performed with high efficiency. In addition, in the invention, it is preferable that the combustion oxidizer, which is supplied to the biomass gasification furnace, be a mixture of air and steam or oxygen and steam.

In addition, as illustrated in FIG. 5, in a methanol production system 30B of a modification example of the third embodiment, a reformation reactor 36 reforming the boosted gas 32 after boosting is provided and the methane concentration, which does not contribute to the methanol synthesis with reformation of the gas, is decreased thereby improving methanol synthesis yield.

REFERENCE SIGNS LIST

10A to 10C biomass gasification gas purification system
11 biomass
12 biomass gasification furnace
13 biomass gasification gas (including tar component)
14 dust removal apparatus
15 desulfurization apparatus
16 pre-reformation reactor
16A to 16C first to third pre-reformation reactors
16a to 16c first to third catalyst sections
20 steam

The invention claimed is:

1. A biomass gasification gas purification method comprising:
   filtering soot and dust from biomass gasification gas obtained through the gasification of the biomass using a biomass gasification furnace;
   removing sulfur oxide component in the filtered biomass gasification gas;
   extracting a part of the biomass gasification gas after desulfurization;
   reforming the tar component in the biomass gasification gas after desulfurization using at least two or more pre-reforming reactors;
   cooling the part of the biomass gasification gas by using a cooler; and
   supplying the cooled biomass gasification gas between the pre-reformation reactors respectively.

2. A methanol production method comprising:
   purifying biomass gasification gas using the biomass gasification gas purification method according to claim 1;
   boosting the biomass gasification gas after pre-reforming; and
   synthesizing the methanol using the boosted gas after boosting.

3. The methanol production method according to claim 2, further comprising:
   reforming the boosted gas after boosting.

* * * * *